United States Patent [19]
Hammer

[11] Patent Number: 5,314,221
[45] Date of Patent: May 24, 1994

[54] APPARATUS FOR AIDING PERSONS, PARTICULARLY HANDICAPPED PERSONS, IN MOVING UNREACHABLE OBJECTS

[75] Inventor: Nicholas A. Hammer, DuBois, Pa.

[73] Assignee: Help Yourself Designs, Incorporated, DuBois, Pa.

[21] Appl. No.: 25,791

[22] Filed: Mar. 3, 1993

[51] Int. Cl.$^5$ .......................... A47B 95/02; B25J 1/04
[52] U.S. Cl. .................. 294/19.1; 16/114 R; 294/1.1
[58] Field of Search ............ 294/1.1, 12, 15, 18, 294/19.1, 22, 24, 26, 86.4, 90, 93, 145, 158; 16/110 R, 110 A, 111 R, 112, 114 R, 114 A, 121, 124; 49/460, 461; 292/262, 336.3, 347; 403/3, 4, 353, 361, 375, 381

[56] References Cited

U.S. PATENT DOCUMENTS

| | | |
|---|---|---|
| Re. 18,069 | 5/1931 | Drumm . |
| 152,866 | 7/1874 | Preater . |
| 252,143 | 1/1882 | Ross . |
| 306,188 | 10/1884 | Strong .................. 294/19.1 X |
| 377,457 | 2/1888 | Horne .................. 16/124 X |
| 603,857 | 5/1898 | Perrote . |
| 648,983 | 5/1900 | Niemeyer . |
| 686,733 | 11/1901 | Houlahan ............... 294/19.1 X |
| 707,669 | 8/1902 | Young . |
| 749,753 | 1/1904 | Soisson . |
| 750,956 | 2/1904 | Essig .................. 294/19.1 X |
| 1,035,483 | 8/1912 | Scott .................. 16/114 R |
| 1,096,630 | 5/1914 | Koehler . |
| 1,143,360 | 6/1915 | Chorvath ............... 16/114 R |
| 1,437,509 | 12/1922 | Genth .................. 16/124 |
| 1,540,358 | 6/1925 | Maurer ................. 16/114 A |
| 1,549,044 | 8/1925 | Rader . |
| 1,707,231 | 4/1929 | Morin . |
| 2,370,860 | 3/1945 | Hanke .................. 16/114 A |
| 2,494,159 | 1/1950 | Bernstein .............. 16/114 A |
| 2,537,750 | 1/1951 | Gretschel . |
| 3,044,659 | 7/1962 | Tupper ................. 16/114 A X |
| 3,107,389 | 10/1963 | Engelbrecht ........... 16/124 |
| 3,556,577 | 1/1971 | Brasseur .............. 294/15 X |
| 3,764,175 | 10/1973 | Yavitch . |
| 3,819,221 | 6/1974 | O'Connor . |
| 3,953,065 | 4/1976 | Shannon ............... 294/1.1 |
| 4,622,868 | 11/1986 | Flannigan . |
| 4,726,263 | 2/1988 | Lake . |

FOREIGN PATENT DOCUMENTS 853340 10/1952 Fed. Rep. of Germany ..... 294/19.1

Primary Examiner—Johnny D. Cherry

[57] ABSTRACT

A ball and socket arrangement for aiding the handicapped or persons having limited reach or mobility and including one of a plurality of socket elements secured to an object which is to be moved and which is engageable by means of a manually grippable wand including an elongated handle having a ball at one end which is adapted to engage the socket to apply either a pulling or a pushing force thereto and wherein the angle and orientation of the sockets varies depending upon the object to which the socket is attached and which may be, for example, a drawer, door, slidable shelf, or the like.

15 Claims, 6 Drawing Sheets

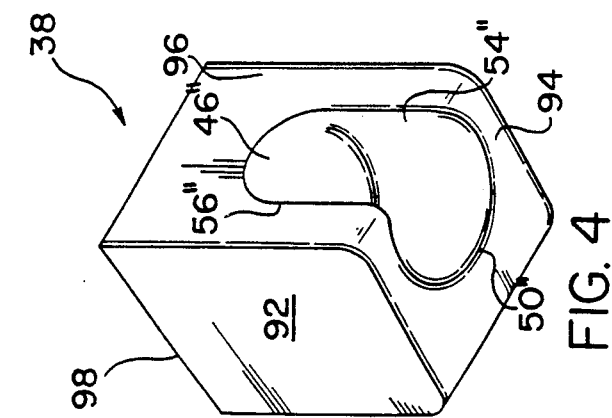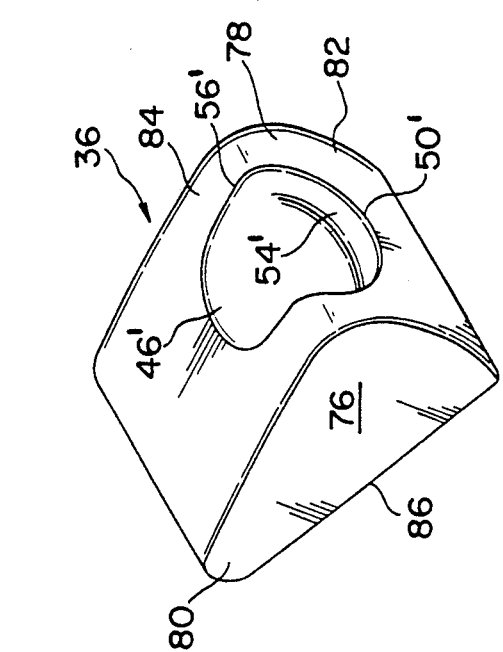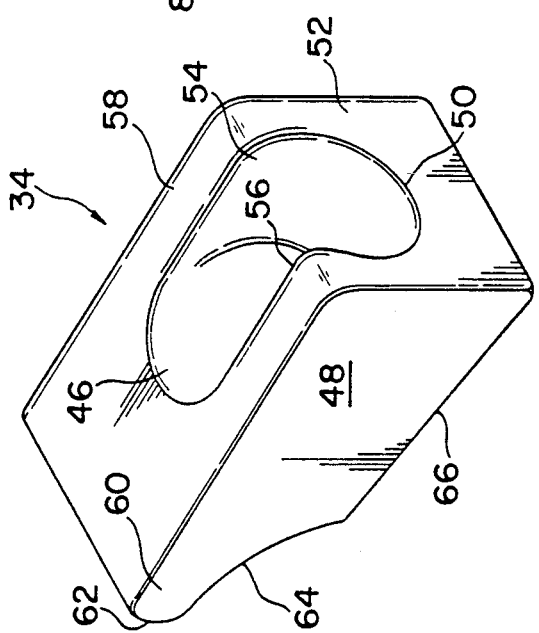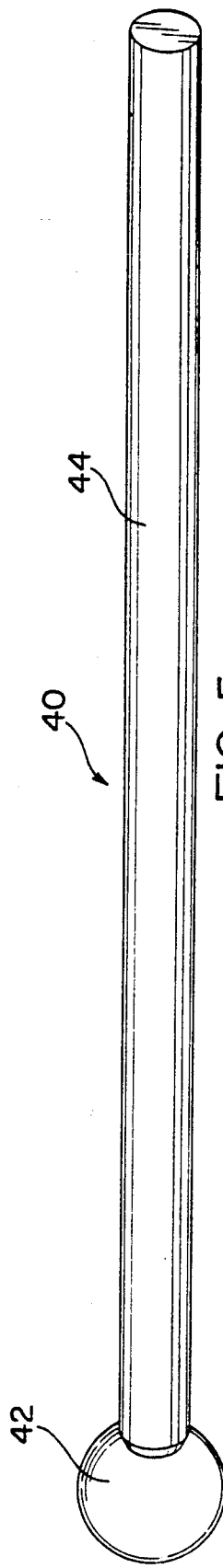

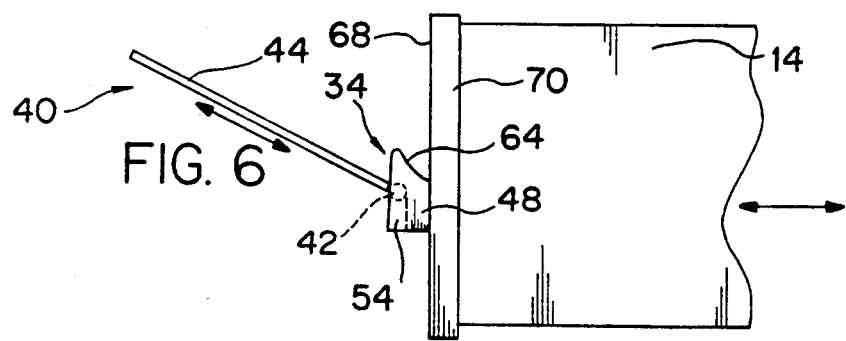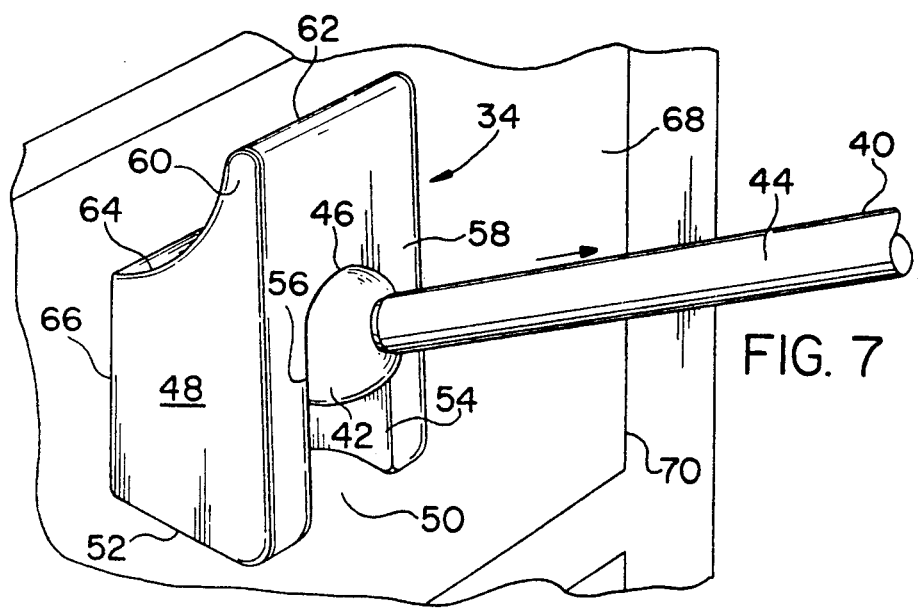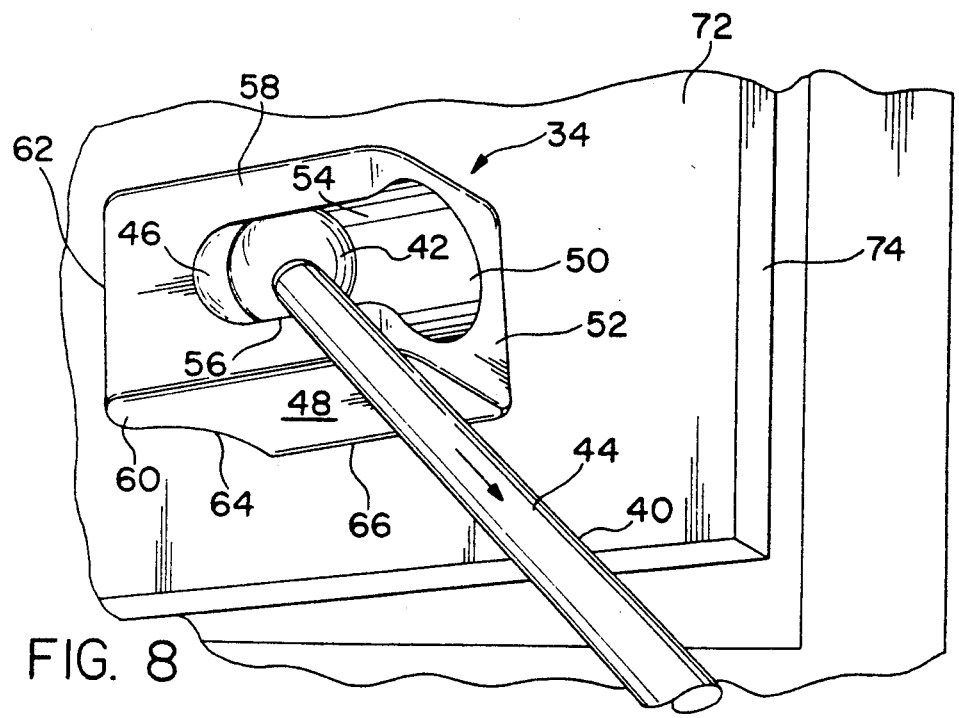

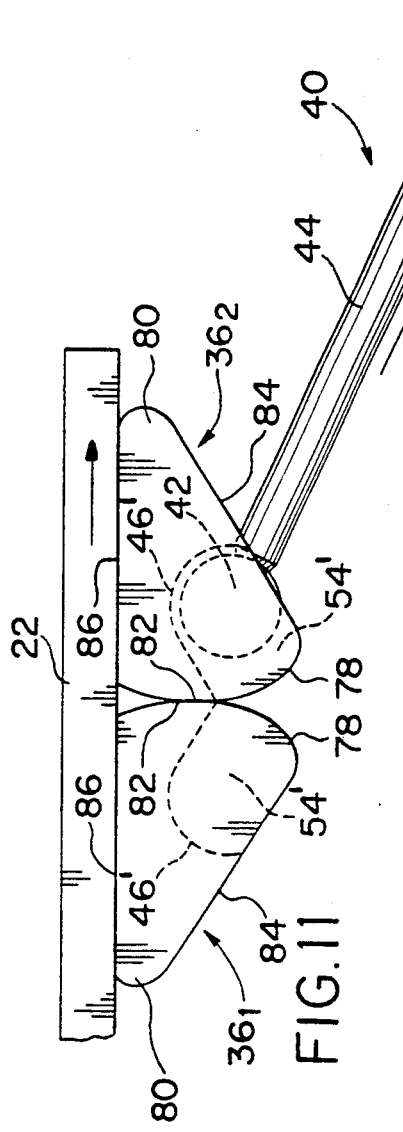

APPARATUS FOR AIDING PERSONS, PARTICULARLY HANDICAPPED PERSONS, IN MOVING UNREACHABLE OBJECTS

BACKGROUND OF THE INVENTION

This invention relates generally to apparatus for providing a mechanical advantage, and more particularly to manually gripped apparatus for aiding persons having limited reach and mobility, such as the handicapped, to move an object such as a drawer, a movable shelf, a door, or the like.

Various types of implements for extending the reach of a person are generally known and cover a wide spectrum of tools and mechanical devices depending upon their intended use. One group of implements is directed to cooking utensils which, for example, have detachable handles for lifting and moving a cooking utensil from one place to another. Another group includes those having a relatively long handle with a manipulator at one end, such as tools for enabling a driver of an automobile, for example, to operate a door lock or turn a window crank. Also known are such devices as farm tool implements and mechanic's tools which include interchangeable tools at one end thereof. However, none of the prior art teaches or suggests apparatus for aiding people in wheelchairs or who are handicapped in ways which impede their reach or mobility to gain access to a drawer, door, window, or the like.

It is a primary object of the subject invention, therefore, to provide a system of mechanical components for aiding the handicapped.

It is a further object of the invention to provide apparatus for aiding persons with limited reach or mobility.

It is another object of the invention to provide a system of mechanical components for enabling people in wheelchairs or who are handicapped in ways which impede their reach or mobility to gain access to an otherwise inaccessible location.

Briefly, the foregoing and other objects are achieved by a ball and socket arrangement including one of a plurality of socket elements secured to an object which is to be moved and which is engageable by means of a manually grippable wand including an elongated handle having a ball at one end which is adapted to engage the socket to apply either a pulling or a pushing force thereto and wherein the angle and orientation of the sockets varies depending upon the object to which the socket is attached and which may be, for example, a drawer, door, slidable shelf, or the like.

BRIEF DESCRIPTION OF THE DRAWINGS

The details of the invention will be more readily understood when considered in conjunction with the accompanying drawings wherein:

FIGS. 2, 3 and 4 are perspective views generally illustrative of three preferred embodiments of a socket member forming one part of the subject invention;

FIG. 5 is a perspective view of a wand for engaging the socket members shown in FIGS. 2, 3 and 4 and which forms the other part of the subject invention;

FIGS. 6 and 7 are illustrative of the wand shown in FIG. 5 and the socket member shown in FIG. 2 for use as a drawer pull and which is further shown in FIG. 1;

FIG. 8 is a variation of the arrangement shown in FIG. 6 for use as a door opener;

FIGS. 10 and 11 are side elevational views further illustrative of the configuration shown in FIG. 9 being pushed and pulled, respectively;

FIG. 12 is a side elevational view partially in phantom illustrating a modified version of the configuration shown in FIG. 9;

DETAILED DESCRIPTION OF THE INVENTION

Figure 1:
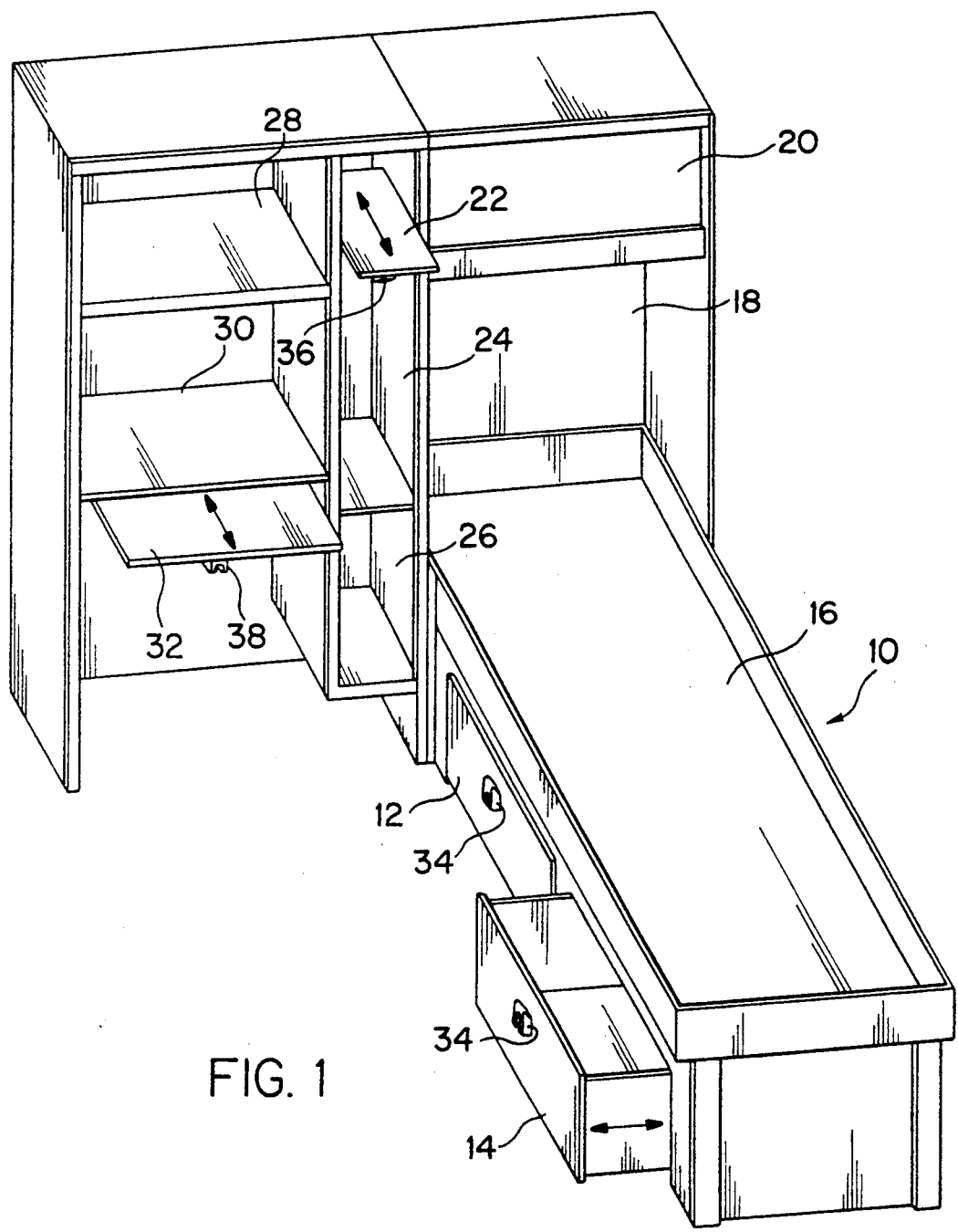
FIG. 1 is a perspective view generally illustrative of an arrangement of furniture utilizing the subject invention.

Referring now to the drawing figures wherein like reference numerals refer to like parts throughout, attention is first directed to FIG. 1 where there is shown a modular assembly of furniture including the preferred embodiments of the invention and which are designed to be used by persons who are handicapped, such as by persons restricted to wheelchairs or the like.

FIG. 1, for example, depicts the combination of a trundle type bed structure 10 having a pair of pull-out drawers 12 and 14 located below a bed frame 16, a backboard 18, including an upper storage compartment 20, and an adjoining open closet area including an upper pull-out shelf member 22 which may, when desired, include a hanger rack, not shown. Also shown are a pair of lower vertically oriented storage spaces 24 and 26, a generally rectangular upper storage compartment 28 and a lower desk or work area 30 including a pull-out shelf 32.

What is significant about the arrangement shown in FIG. 1 is that the pull-out drawers 12 and 14 include respective socket members 34 which are shown in FIG. 2, the upper pull-out shelf 22 includes a pair of back to back socket members 36 as shown in FIG. 3, and the pull-out desk shelf 32 includes a socket member 38 as shown in FIG. 4. While the socket members 34, 36 and 38 thus comprise three separate embodiments, what they all have in common is a recessed socket 46, 46' and 46" in a slotted bore 54, 54' and 54" which is sized to fit and be engaged by the ball 42 of the wand 40, shown in FIG. 5.

Considering now the details of the socket members 34, 36 and 38, the member 34 shown in FIG. 2 is particularly adapted to be used as a drawer pull and is comprised of a generally rectangular block type body member 48 having a circular opening 50, sized to accept the ball 42 of a wand 40, formed through one end surface 52. A circular cylindrical bore 54, is formed in the body of the block to a predetermined depth where it terminates in the socket 46. A linear slot 56 into the bore 54 extends lengthwise from the opening 50 to the socket 46. The width of the slot 56 is less than the diameter of the ball 42 so that the wand 40 cannot be pulled therefrom, but can only enter and be removed from the opening 50. This also applies to the slots of other socket members 36 and 38 to be subsequently described.

The opposite end of the block 48 comprises a relatively narrow end region 60 having a rounded end surface 62 which extends into a curved surface 64 which terminates in a rear surface portion 66. The narrow upper region 60 permits the member 34 to be manually grasped in addition to its engagement with the wand 40.

As shown in FIGS. 6 and 7, the rear surface 66 of the socket member 34 (FIG. 2) is fastened or otherwise secured to the front surface 68 of, for example, the front panel 70 of a drawer 14 as shown in FIG. 1, or it may be applied to the front surface 72 of a hinged door 74, or the like as shown in FIG. 8. FIGS. 7 and 8 depict two mutually orthogonal orientations and thus two separate uses of the socket member 34 shown in FIG. 2.

Considering now the socket member 36 shown in FIG. 3, it is comprised of a generally wedge-shaped body 76 having an enlarged rounded front end region 78 and smaller rear end region 80 and which includes a cylindrical bore 54' of relatively shorter depth formed therein which is open on the front and top faces 82 and 84, and which terminates at the socket 46'. The body 76 additionally includes a substantially flat rear mounting surface 86.

Figure 9:
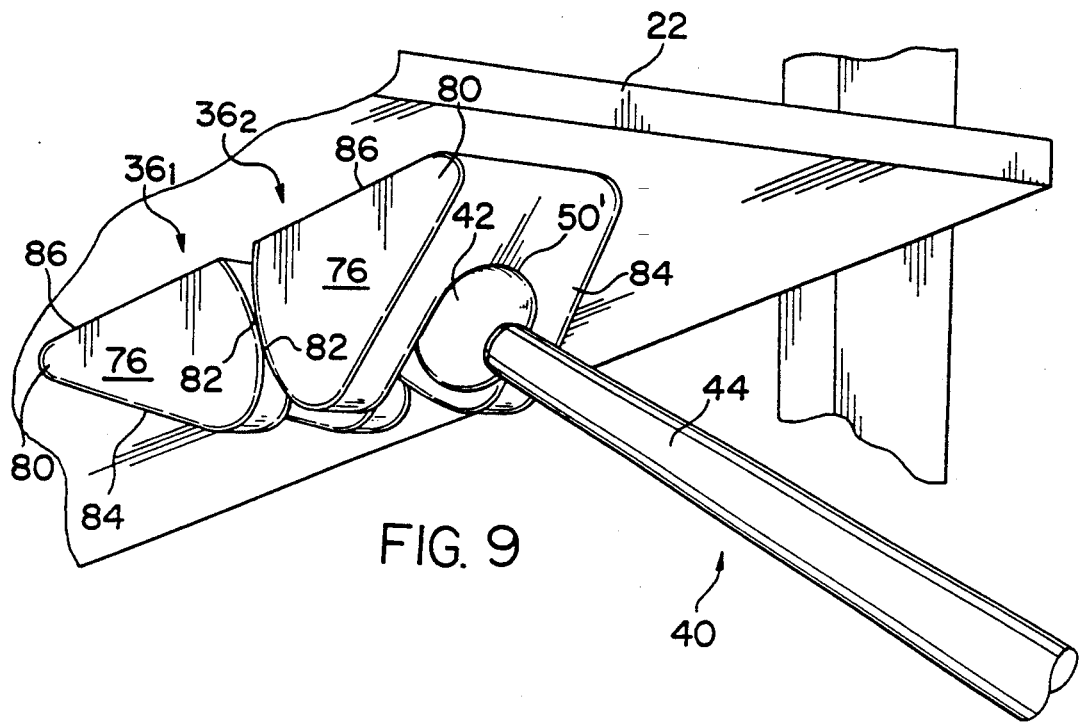
FIG. 9 is a perspective view illustrative of a pair of socket members shown in FIG. 3 arranged back to back and utilized in combination with the wand shown in FIG. 5 for actuating an elevated slidable shelf as shown in FIG. 1.
Figure 10:
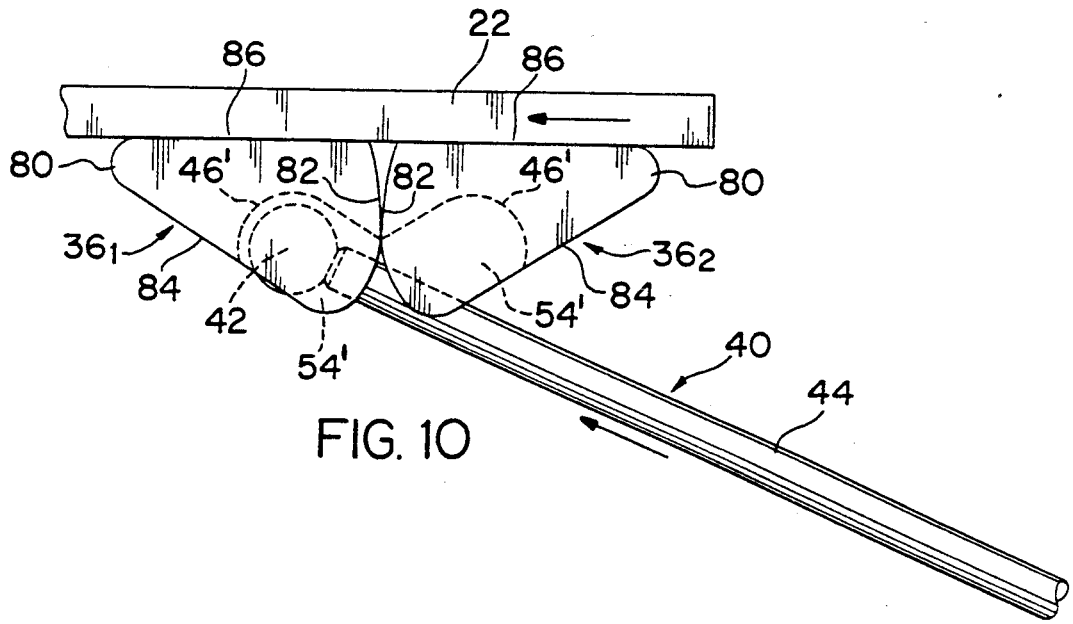

As shown in FIGS. 9, 10 and 11, a pair of socket members $36_1$ and $36_2$ are arranged in back-to-back relationship on a panel member, which may be, for example, the slidable shelf 22 shown in FIG. 1. The two members $36_1$ and $36_2$ are positioned so that their respective enlarged end portions 78 face one another, with the end surfaces 82 abutting one another.

As shown in FIGS. 10 and 11, the respective bores 54' of the socket member $36_1$ and $36_2$ intersect each other providing a pair of mutually opposed sockets 46'. Thus, as depicted in FIG. 10, when the wand 40 is inserted in the rear member $36_1$ and a pushing motion is imparted thereto, the shelf 22 is forced to move to the left or to the rear as shown in FIG. 1. Alternatively, when the wand 40 is placed in the front pull $36_2$ and a pulling motion is exerted on the wand shaft 44 as shown in FIG. 11, the member 22 will be moved to the right or outwardly as shown in FIG. 1.

A modification of the configuration of the two socket members $36_1$ and $36_2$, as shown in FIG. 9, may be resorted to when desirable by utilizing a composite socket member 36' (FIG. 12) which is comprised of a unitary body member 88 having a common opening 90 and a pair of opposing bores $54_1$ and $54_2$ which terminate in respective sockets $46_1$ and $46_2$. With the positioning of the ball element 42 of the wand 40 in either socket $46_1$ or $46_2$, fore and aft or left or right motion can be imparted to the member 22 as before.

Considering now the third socket member 38, it comprises a generally square or rectangular body 92 as shown in FIG. 4. It includes a circular cylindrical bore 54" having a front opening 50" formed in the relatively flat front end wall surface 94 and which is open to the side wall 96 by the slot 56" and terminating in a rearwardly located socket 46" as in the other embodiments shown in FIGS. 2 and 3.

The depth of the bore 54' is substantially the same as that in the socket member 34 of FIG. 2. The opposite or rear end wall surface 98 is slightly angulated relative to the front wall surface 94 such that when it is mounted on the bottom surface of a slidable member such as the sliding desk panel 32 shown in FIG. 1, it can pulled out and pushed in by means of the wand 40.

Figure 13:
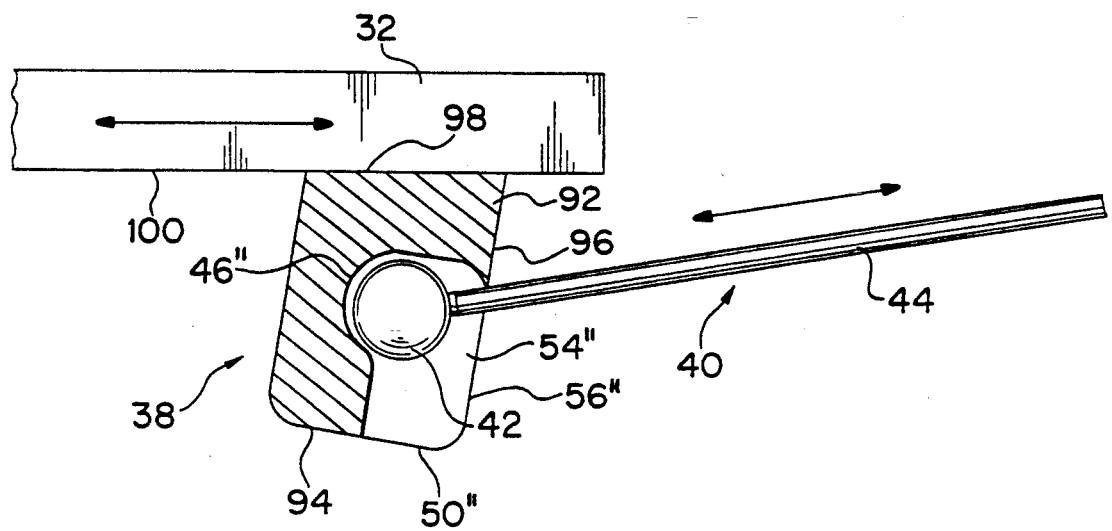
FIG. 13 is a side elevational view partially in section of the members shown in FIGS. 4 and 5 for pulling out and pushing back a desk panel as shown in FIG. 1.
Figure 14:
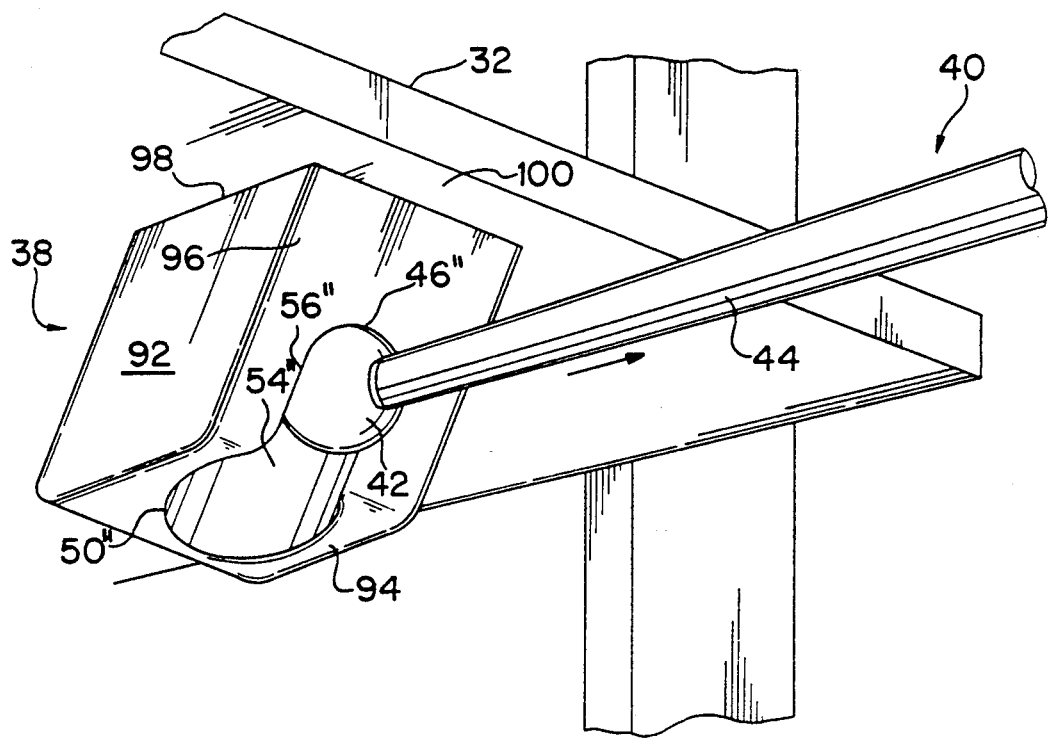
FIG. 14 is a perspective view further illustrative of the configuration shown in FIG. 12.

Referring briefly to FIGS. 13 and 14, the socket member 38 is shown mounted on the bottom surface 100 of the desk panel 3 such that it tilts slightly to the rear, with the ball element 42 of the wand 44 entering and leaving the bore 54" and the slot 56" from the bottom.

It should be noted that the mounting surfaces 66 and 98 of the socket member 34 (FIG. 2) and socket member 38 (FIG. 4) need not be angulated with respect to its opposing wall surface and can, when desirable, be parallel therewith or even tilted forward. Also, the elements shown in FIGS. 2, 3 and 4 can be applied to other types of movable furniture components as well as windows and doors.

Thus, what has been shown and described is a relatively simple yet effective access arrangement comprised of a plurality of socket elements which are engageable with a single ball element located at the end of a wand and where the angle and orientation of the sockets varies and is dependent upon the object to which the socket is attached.

Having thus shown and described what is at present considered to be the preferred embodiments of the invention, it should be noted that the same has been made by way of illustration and not limitation. Accordingly, all modifications, alterations and changes coming within the scope of the invention as set forth in the appended claims are meant to be included.

I claim:

1. Apparatus for aiding persons and particularly handicapped persons, in moving objects which are out of reach, comprising:

a socket type body member secured to an object which is to be moved, said body member comprising a generally rectangular block type body member including a region of reduced thickness at one end and including a circular cylindrical bore formed in the other end of said body member, said bore having a front opening formed and terminating in a socket for receiving actuating means, said body member further having a slot formed in a surface adjacent said front opening into the bore, said slot extending lengthwise from said front opening to said socket; and a wand type member comprising said actuating means and including an elongated handle and a ball type element at one end for engaging the socket of said body member;

said circular cylindrical bore further having a diameter at least equal to the diameter of said ball type element, said wand type member being freely movable through said bore between said front opening and said socket with the handle of said wand type member passing through said slot;

whereby a person manually grips the handle of the wand type member, engages the socket via said ball type element, and applies a force thereto for moving said object and thereafter disengages the ball type element from the socket following a desired movement of said object.

2. The apparatus as defined by claim 1 wherein said block type body member includes a generally flat mounting surface opposite said slot.

3. The apparatus as defined by claim 2 wherein said mounting surface is inclined relative to said surface having said slot formed therein.

4. The apparatus as defined by claim 1 wherein said slot includes a width dimension thereacross which is less than the diameter of said ball type element, whereby said wand type element cannot be removed from or inserted into the socket and the bore except by way of said front opening.

5. Apparatus for aiding persons and particularly handicapped persons, in moving objects which are out of reach, comprising:

a socket type body member secured to an object which is to be moved, said body member comprising a generally rectangular block type body member including a front surface located at one end and a generally flat rear mounting surface at an end opposite said front surface and including a circular cylindrical bore formed in said front surface, said bore terminating in a socket for receiving actuating means, said body member further having a slot formed in a surface adjacent said front opening into the bore, said slot extending lengthwise from said front opening to said socket; and a wand type member comprising said actuating means and including an elongated handle and a ball type element at one end for engaging the socket of said body member, said circular cylindrical bore further having a diameter at least equal to the diameter of said ball type element said wand type member being freely movable through said bore between said front opening and said socket with the handle of said wand type member passing through said slot;

whereby a person manually grips the handle of said wand type member, engages the socket via said ball type element, and applies a force thereto for moving said object and thereafter disengages the ball type element from the socket following a desired movement of said object.

6. The apparatus as defined by claim 5 wherein said rear mounting surface is inclined relative to said front surface.

7. The apparatus as defined by claim 5 wherein said slot includes a width dimension thereacross which is less than the diameter of said ball type element, whereby the wand type member cannot be removed from or inserted into the socket and the bore except by way of said front opening.

8. Apparatus for aiding persons and particularly handicapped persons, in moving objects which are out of reach, comprising:

a socket type body member secured to an object which is to be moved, said body member comprising at least one generally wedge shaped body member including a circular cylindrical bore formed in one larger end of said body member, said bore having a front opening formed therein and terminating in a socket for receiving actuating means, said body member further having a slot formed in a surface adjacent said front opening into the bore, said slot extending lengthwise from said front opening to said socket means; and a wand type member comprising said actuating means and including an elongated handle and a ball type element at one end for engaging the socket of said body member, said circular cylindrical bore further having a diameter at least equal to the diameter of said ball type element, said wand type member being freely movable through said bore between said front opening and said socket with the handle of said wand type member passing through said slot;

whereby a person manually grips the handle of the wand type member, engages the socket via said ball type member, and applies a force thereto for moving said object and thereafter disengages the wand type member from the socket following a desired movement of said object.

9. The apparatus as defined by claim 8 wherein said body member includes one end region of increased thickness relative to an opposite end region and wherein said bore, said slot and said socket are located in said one end region.

10. The apparatus as defined by claim 9 and wherein said body member includes a generally flat rear mounting surface extending from said one end region to said opposite end region.

11. The apparatus as defined by claim 8 and wherein said body member includes a pair of said generally wedge shaped body members positioned in mutually end to end relationship.

12. The apparatus as defined by claim 11 wherein one end region of said pair of body members abut one another.

13. The apparatus as defined by claim 8 wherein said slot includes a width dimension thereacross which is less than the diameter of said ball type element, whereby the wand type member cannot be removed from or inserted into the socket and the bore except by way of said front opening.

14. Apparatus for aiding persons and particularly handicapped persons, in moving objects which are out of reach, comprising:

a socket type body member secured to an object which is to be moved, said body member comprising a unitary body member having a pair of opposing cylindrical bores and respective slots joined by a common front opening and wherein said bores terminate in respective sockets spaced apart from said common opening for receiving actuating means, said body member further having respective slots formed in a surface adjacent said front opening into the bores, each of said respective slots extending lengthwise from said front opening to said respective sockets; and a wand type member comprising said actuating means and including an elongated handle and a ball type element at one end for selectively engaging one of said sockets of said body member, said circular cylindrical bores each having a diameter at least equal to the diameter of said ball type element, said wand type member being freely movable through said bores between said front opening and a selected one of said sockets with the handle of said wand type member passing through said slots;

whereby a person manually grips the handle of the wand type member, engages one of the sockets via said ball type member, and applies a force thereto for moving said object and thereafter disengages the wand type member from the said one socket following a desired movement of said object.

15. The apparatus as defined by claim 14 wherein each of said slots include a width dimension thereacross which is less than the diameter of said ball type element, whereby the wand type member cannot be removed from or inserted into the socket and the bore except by way of said front opening.

* * * * *